United States Patent [19]

Akimune et al.

[11] 4,338,356

[45] Jul. 6, 1982

[54] METHOD OF PRODUCING FLAT SOLID ELECTROLYTE LAYER OF FLAT FILM TYPE OXYGEN SENSOR

[75] Inventors: Yoshio Akimune, Yokohama; Satoshi Ambe, Yokosuka; Hiroshi Takao, Kamakura; Shinji Kimura, Yokohama, all of Japan

[73] Assignee: Nissan Motor Company, Limited, Yokohama, Japan

[21] Appl. No.: 169,031

[22] Filed: Jul. 15, 1980

[30] Foreign Application Priority Data

Jul. 16, 1979 [JP] Japan .................................. 54-89243

[51] Int. Cl.³ ..................................... B05D 5/12
[52] U.S. Cl. ................................. 427/123; 427/126.3; 427/376.2; 427/376.6; 427/380; 427/383.3; 427/404; 427/403; 427/419.2; 427/419.3; 204/195 S
[58] Field of Search .................. 427/126.3, 403, 376.2, 427/376.6, 380, 383.3, 404, 419.2, 419.3, 419.4, 123; 204/195 S

[56] References Cited

U.S. PATENT DOCUMENTS 3,843,400 10/1974 Radford et al. ..................... 429/152
4,040,929 8/1977 Bauer et al. ...................... 204/195 S
4,107,019 8/1978 Takao et al. ...................... 204/195 S
4,209,378 6/1980 Shinohara et al. ............... 204/195 S
4,210,509 7/1980 Obayasi et al. .................. 204/195 S

FOREIGN PATENT DOCUMENTS 2742279 3/1978 Fed. Rep. of Germany .
2852638 6/1980 Fed. Rep. of Germany .
2045054 2/1971 France .

Primary Examiner—Norman Morgenstern
Assistant Examiner—R. Bueker
Attorney, Agent, or Firm—Schwartz, Jeffery, Schwaab, Mack, Blumenthal & Koch

[57] ABSTRACT

A method of producing a flat solid electrolyte layer of a flat film type oxygen sensor is disclosed. The method comprises in steps, (a) preparing first and second electrolyte pastes each containing stabilizer, the content of stabilizer in the first electrolyte paste being smaller than that in the second electrolyte paste, (b) applying the first electrolyte paste onto an electrode layer and then applying the second electrolyte paste onto the outer face of the first electrolyte paste to form a layered paste heap on the electrode layer, and (c) firing the layered paste heap to form a solid electrolyte layer on the electrode layer. With this production method, the stabilizer is uniformly and homogeneously distributed into the body of the fired electrolyte layer.

14 Claims, 7 Drawing Figures

METHOD OF PRODUCING FLAT SOLID ELECTROLYTE LAYER OF FLAT FILM TYPE OXYGEN SENSOR

FIELD OF THE INVENTION

The present invention relates in general to an oxygen sensor for measuring the oxygen concentration in a fluid, the sensor being of the type having a layer of an oxygen ion conductive solid electrolyte. More specifically, the present invention is concerned with a method of forming a so-called flat film type oxygen sensor which is suitable for measuring the oxygen concentration in an engine exhaust gas.

BACKGROUND OF THE INVENTION

It is known that flat film type oxygen sensors which use a flat solid electrolyte layer show better performance in EMF (electromotive force) characteristic and responsiveness as compared with tubular type oxygen sensors which use a tubular solid electrolyte. However, some of such oxygen sensors fail to exhibit their maximum performance because of inhomogeneous distribution of a stabilizer in the body of the solid electrolyte, originating from the inherent production method of the sensors. This drawback encountered in the conventional oxygen sensors will become apparent hereinafter.

SUMMARY OF THE INVENTION

According to the present invention, there is provided a method of producing a flat film type oxygen sensor including an oxygen ion conductive solid electrolyte layer. The method comprises in steps (a) preparing first and second electrolyte pastes each containing stabilizer, the content of stabilizer in the first electrolyte paste being smaller than that in the second electrolyte paste, (b) applying the first electrolyte paste onto an electrode layer and then applying the second electrolyte paste onto the outer face of the first electrolyte paste to form a layered paste heap on the electrode layer, and (c) firing the layered paste heap to form a solid electrolyte layer on the electrode layer.

It is an object of the present invention to provide a method of producing a flat film type oxygen sensor including a flat solid electrolyte layer of which stabilizer is uniformly and homogeneously distributed in the body of the electrolyte layer.

It is another object of the present invention to provide a method which assures production of a flat solid electrolyte layer without formation of cracks therein.

Other objects and advantages of the present invention will become clear from the following description when taken in conjunction with the accompanying drawings.

DESCRIPTION OF PRIOR ART

Prior to describing in detail the invention, an outlined explanation of conventional flat film type oxygen sensor will be made with reference to FIG. 1 in order to clarify the invention.

Figure 1:
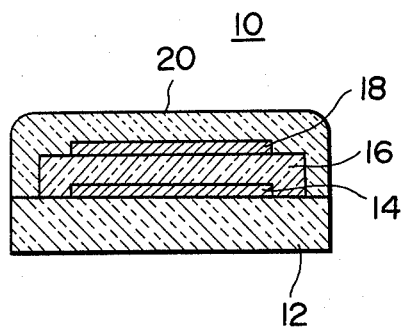
FIG. 1 is a cross section view of a conventionally used flat film type oxygen sensor.

Referring to FIG. 1 of the drawings, there is shown a conventional flat film type sensor which is designated by numeral 10. The sensor 10 generally comprises a partition layer 12 of ceramics designed to serve as a structurally basic member of the sensor 10, a first or reference electrode layer 14 deposited on the partition layer 12, a layer 16 of an oxygen ion conductive solid electrolyte deposited on the first electrode layer 14, a second or measurement electrode layer 18 deposited on the solid electrolyte layer 16, and a protective layer 20 covering both the second electrode layer 18 and side surfaces of the solid electrolyte layer 16 entirely and intimately, as shown. Usually, such sensor as mentioned above is produced by taking the following production process.

To produce the sensor 10, a platinum paste is applied or painted onto a surface of a sintered alumina sheet 12, and then the heaped paste on the sheet 12 is air-dried and then fired to form the first or reference electrode layer 14 on the sheet 12. An electrolyte paste composed of a certain amount of powdered electrolyte material containing a certain amount of stabilizer, and a certain amount of organic vehicle is applied or painted onto the fired electrode layer 14, and then the heaped electrolyte paste is air-dried and then fired to form the solid electrolyte layer 16. Then, the same platinum paste as producing the first electrode layer 14 is applied or painted onto the fired electrolyte layer 16, and the heaped platinum layer on the layer 16 is air-dried and then fired to form the second or measurement electrode layer 18. Finally, a protective layer material such as powdered calcium zirconate is deposited on the entire front surface of the multi-layered article by plasma spraying technique to form the porous protective layer 20.

Hitherto, the application of the electrolyte paste onto the reference electrode layer 14 has been made by a screen-printing method in which for obtaining the desired thickness of the electrolyte paste heap, several coats are repeatedly applied to the first electrode layer 14. However, in this production method, it has been revealed that emission of the stabilizer which inevitably occurs at the firing process of the electrolyte paste causes inhomogeneous distribution of components of the electrolyte in the direction of the thickness of the same, with the result that the oxygen ion conductivity of the solid electrolyte 16 thus produced lowers considerably thereby to decrease the output characteristic of the oxygen sensor.

Therefore, elimination of this drawback is an essential object of the present invention.

DESCRIPTION OF THE INVENTION

As will become clear as the description proceeds, the feature of the present invention resides in that for deposition of the electrolyte paste on the first or reference electrode layer, several kinds of electrolyte paste which contain different amounts of stabilizer are painted onto one over another so that upon completion of firing of the multi-layered paste heap, even or uniform distribution of the stabilizer is obtained in the fired solid electrolyte.

For putting the concept of the invention into practical use, several experiments were carried out.

EXPERIMENT

For studying the amount of lost stabilizer of the produced electrolyte layer with respect to the firing condition of the electrolyte paste, several test samples were prepared. Each sample was produced by applying via "screen-printing method" an electrolyte paste composed of a certain amount of powdered $Y_2O_3$-$ZrO_2$ and a certain amount of organic vehicle onto a suitable sheet member, air-drying and firing the paste on the sheet member. Then, the samples thus produced were subjected to several evaluation tests. The results of these tests are shown in Tables I, II and III.

TABLE I

| Firing Temperature (°C.) | $Y_2O_3$ reduction rate at the outer surface of the solid electrolyte (%) |
| --- | --- |
| 1300 | 31 |
| 1400 | 36 |
| 1500 | 44 |
| 1600 | 56 |

TABLE II

| Firing time for which the electrolyte paste was fired (hours) | $Y_2O_3$ reduction rate at the outer surface of the solid electrolyte (%) |
| --- | --- |
| 0 | 31 |
| 2 | 36 |
| 4 | 40 |
| 6 | 45 |
| 8 | 50 |

TABLE III

| Distance from the outer surface of the solid electrolyte layer (μm) | $Y_2O_3$ reduction rate (%) |
| --- | --- |
| 0 | 36 |
| 5 | 18 |
| 10 | 8 |
| 15 | 4 |
| 20 | 0 |

Table I depicts the reduction rate of the stabilizer ($Y_2O_3$) at the surface of the solid electrolyte layer with respect to the temperature at which the electrolyte paste was fired for two hours. As will be seen from this table, the $Y_2O_3$ reduction rate becomes greater as the firing temperature increases. Table II shows the relationship between the reduction rate of the stabilizer ($Y_2O_3$) at the surface of the fired solid electrolyte layer and the firing time for which the electrolyte paste was fired at a temperature of 1400° C. As will be known from this table, the emission degree of the stabilizer ($Y_2O_3$) in the electrolyte layer becomes greater as the firing time increases. Further, it will be noted that considerable degree of emission of the stabilizer occurs at the initial stage of the firing process. Table III shows the relationship between the distance from the outer surface of the solid electrolyte layer and $Y_2O_3$ reduction rate at the position, on a sample which was produced by firing the electrolyte paste at a temperature of 1400° C. for two hours. From this table, it will be noted that greatest emission of the stabilizer occurs at the outer surface of the solid electrolyte layer.

From the above, it will be known that the emission of the stabilizer ($Y_2O_3$) takes place inevitably at the firing process. Experiments have further revealed that such undesired emission phenomenon occurs also in a case using CaO or MgO as the stabilizer.

The present invention is provided by taking the above mentioned facts into consideration. As will become apparent hereinafter, the electrolyte layer of the oxygen sensor of the present invention is produced by preparing several kinds of electrolyte paste which have different amounts of stabilizer, and applying these pastes one over another in such a manner that a layer of the layered electrolyte paste thus heaped which may exhibit greater stabilizer emission at the firing process is formed by a paste which contains a larger amount of stabilizer, the heaped electrolyte paste thus prepared being air-dried and then fired. With this production method, even or uniform distribution of the stabilizer is achieved throughout the body of the solid electrolyte produced, so that sufficient oxygen ion conductivity is given to the electrolyte from low temperature to high temperature.

Figure 2:
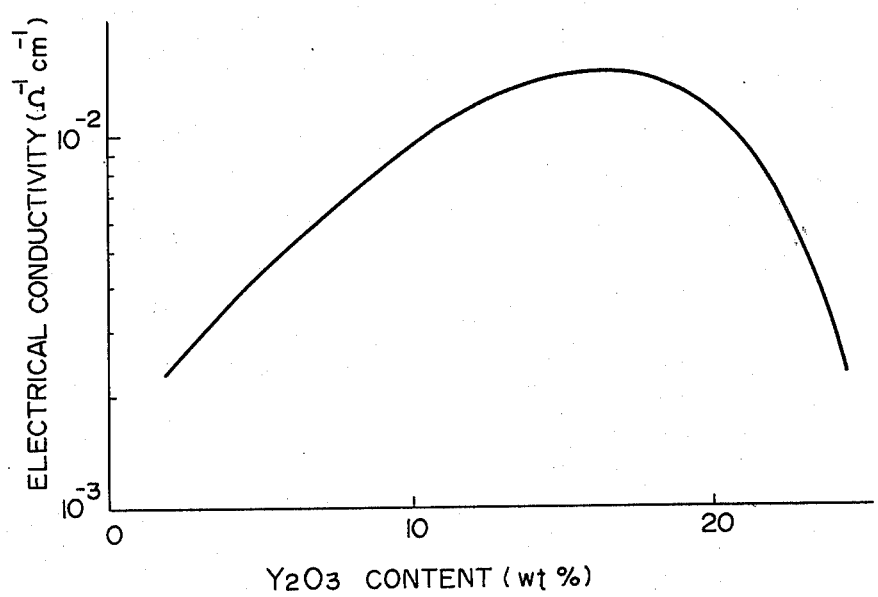
FIG. 2 is a graph depicting the electrical conductivity of $Y_2O_3$-$ZrO_2$ system solid electrolyte with respect to $Y_2O_3$ content in the electrolyte.

FIG. 2 is a graph showing the relationship between $Y_2O_3$ content in a solid electrolyte layer and the electrical conductivity of the electrolyte layer at a temperature of about 800° C., the electrolyte layer being constructed of yttria stabilized zirconia ($Y_2O_3$-$ZrO_2$). As will be seen from this graph, favorable electrical conductivity is achieved within a range from about 2 wt.% to about 23 wt.%. It has been revealed that in using CaO or MgO as the stabilizer, substantially the same result as of using $Y_2O_3$ is given.

From this graph, it will be noted that the stabilizer content should be determined within the range from about 2 wt.% to about 23 wt.%. If the stabilizer content is less than 2 wt.%, the electrical conductivity of the solid electrolyte is greatly decreased as is known from the graph, and if the stabilizer content is greater than 23 wt.%, there occurs severe problem in which the electrolyte layer may be cracked at the firing process.

The present invention will be further illustrated by the following example.

EXAMPLE

Four kinds of electrolyte paste were prepared for making the solid electrolyte layer according to the present invention, these pastes being designated by references No. 1, No. 2, No. 3 and No. 4 in Table-IV. As shown in the Table, each of these pastes was composed of certain amount of $ZrO_2$ stabilized by certain amount of $Y_2O_3$, and organic vehicle (mixture of ethylcellulose and terpineol) which are kneaded together.

TABLE IV

| | Powdered materials of the electrolyte | | organic vehicle | content of the powdered materials (wt. %) |
| --- | --- | --- | --- | --- |
| | $Y_2O_3$ (wt. %) | $ZrO_2$ (wt. %) | | |
| No. 1 | 12 | 88 | ethylcellulose + terpineol | 50 |
| No. 2 | 14 | 86 | ethylcellulose + terpineol | 50 |

TABLE IV-continued

| | Powdered materials of the electrolyte | | organic | content of the powdered materials |
|---|---|---|---|---|
| | Y$_2$O$_3$ (wt. %) | ZrO$_2$ (wt. %) | vehicle | (wt. %) |
| No. 3 | 16 | 84 | ethyl-cellulose + terpineol | 50 |
| No. 4 | 18 | 82 | ethyl-cellulose + terpineol | 50 |

Figure 3:
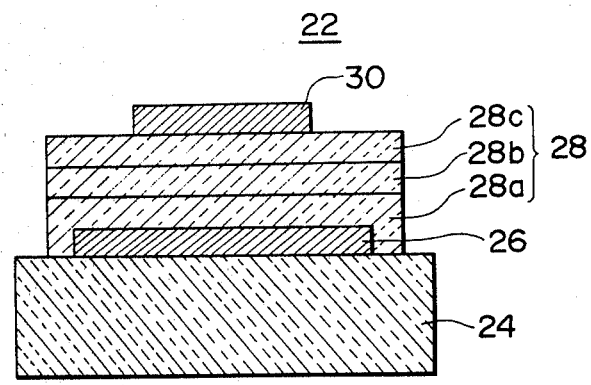
FIG. 3 is a cross section view of a flat film type oxygen sensor which is produced through a method according the present invention.
Figure 4:
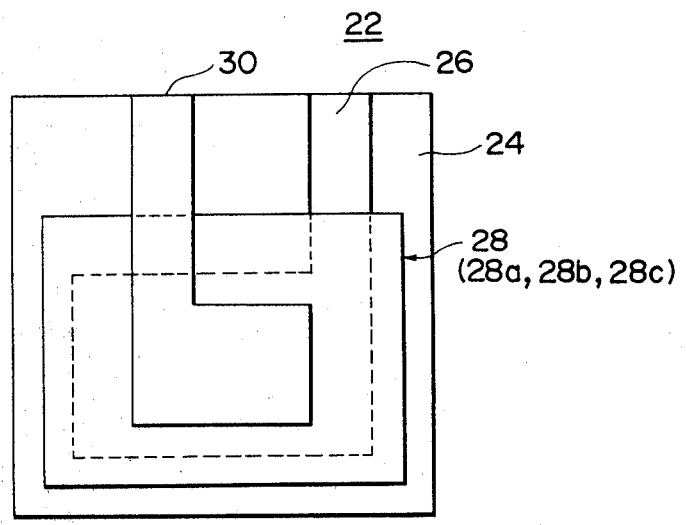
FIG. 4 is a plan view of the sensor of FIG. 3.

Six samples of oxygen sensors A, B, C, D and F each having a construction as illustrated in FIGS. 3 and 4 were produced. Each sensor 22 was produced by taking the following production process.

A platinum paste composed of 70 wt.% powdered platinum and 30 wt.% organic vehicle (such a lacquer thinner) was applied or painted via the screen-printing method onto a sintered alumina sheet 24. The paste on the sheet 24 was air-dried and fired to form a first or reference electrode layer 26. Then, selected three of the pastes described on Table IV were successively applied or painted by means of the screen-printing method onto the electrode layer 26 one over another in such an order as indicated by Table V to form a triple-layered paste heap 28 (28a, 28b and 28c) on the electrode layer 26. The paste heap 28 was air-dried and fired under the conditions indicated by Table V to form a solid electrolyte layer 28. Then, the same platinum paste as producing the reference electrode layer 26 was applied or painted by the screen-printing method onto the solid electrolyte layer 28. The paste heap on the layer 28 was air-dried and then fired to form a second or measurement electrode layer 30.

TABLE V

| Sam-ples | Selected electrolyte pastes | | | Firing condition | Note |
|---|---|---|---|---|---|
| | First coating (28a) | Second coating (28b) | Third coating (28c) | | |
| A | No.4 | No.4 | No.4 | | |
| B | No.3 | No.3 | No.3 | | conventional method |
| C | No.1 | No.1 | No.1 | | |
| D | No.1 | No.1 | No.3 | 1400° C. × 2 hours | method according to the invention |
| E | No.1 | No.1 | No.2 | | |
| F | No.1 | No.2 | No.4 | | |

EXAMINATION I

Figure 5:
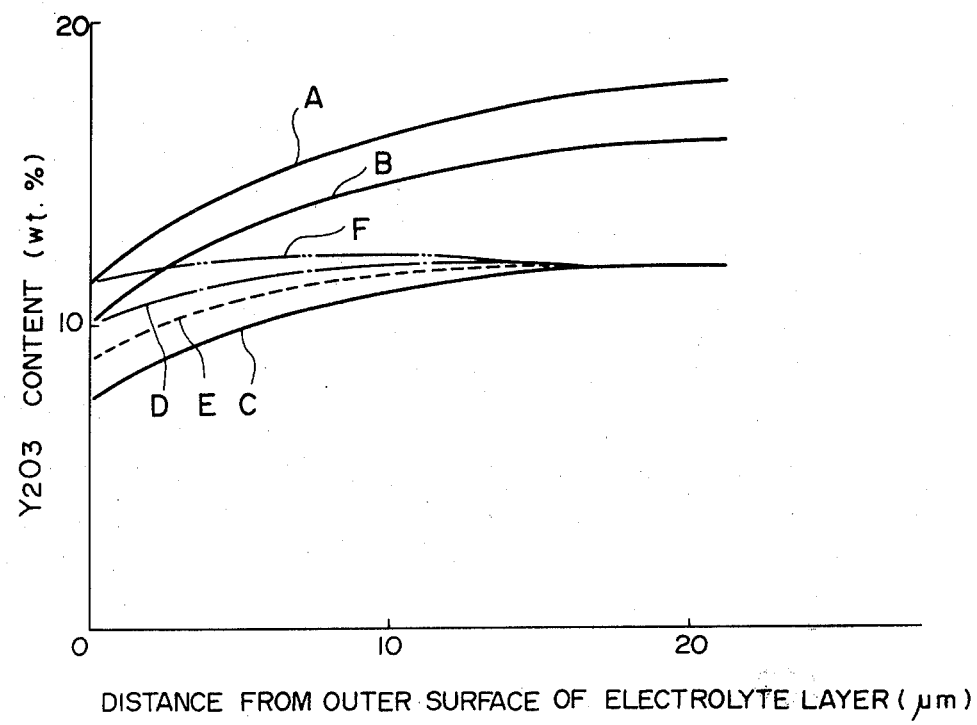
FIG. 5 is a graph showing the relationship between the distance from the outer surface of the solid electrolyte layer and $Y_2O_3$ content in the portion at the distance from the outer surface, on six samples.

The oxygen sensors A, B, C, D, E and F were subjected to a stabilizer distribution test in which the relationship between the distance from the outer surface of the solid electrolyte and Y$_2$O$_3$ content in the portion at the distance from the outer surface was measured on each sensor. The results are shown in the graph of FIG. 5.

As is understood from the graph, in the sensors A, B and C which were produced by conventional method, there is considerable difference in Y$_2$O$_3$ distribution in the direction of the thickness of the electrolyte layer, while in the sensors D, E and F which were produced by the method of the invention, the difference in Y$_2$O$_3$ distribution is smaller than that in the conventional sensors. Now, it should be noted that the solid electrolyte layers of the sensors D, E and F were each produced such that the paste which forms the outermost race 28c of the solid electrolyte layer contains greater amount of Y$_2$O$_3$ than the other two races 28a and 28b, by considering that at firing process of the paste, greater emission of the stabilizer occurs at the outer surface of the solid electrolyte layer. It has been revealed that the sensors D, E and F exhibit excellent stability in generating electromotive force (EMF).

EXAMINATION II

Figure 6:
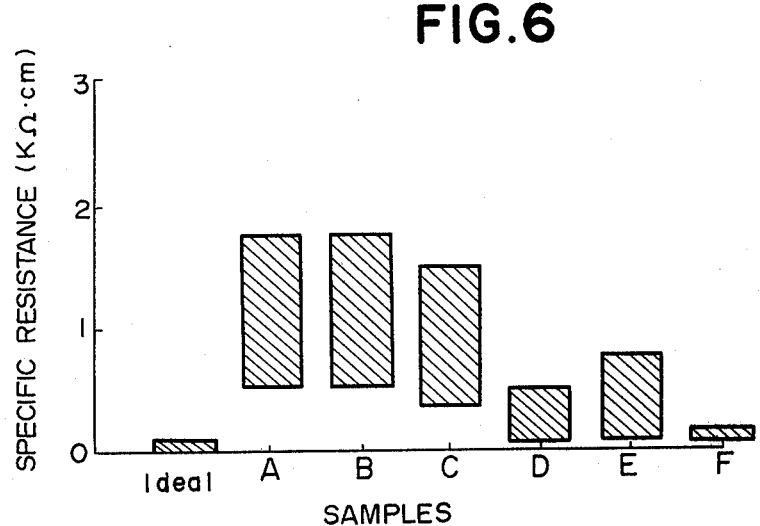
FIG. 6 is a graph showing the specific resistances of the solid electrolyte layers, of the six samples, containing different amounts of $Y_2O_3$.

Specific resistances of the solid electrolyte layers of the sensors were measured. The result is shown in the graph of FIG. 6. As is understood from this graph, in the electrolyte layers of the sensors D, E and F produced by the method of the invention, the specific resistances were considerably low as compared with those of the sensors A, B and C produced by the conventional method. Further, the specific resistance in each sensor D, E or F with respect to measured points was not so greatly dispersed as that of the sensor A, B and C. The desired phenomenon given to the electrolyte layers of the sensors D, E and F brings about decrease in internal resistance loss of these sensors, so that stable generation of electromotive force (EMF) is expected.

EXAMINATION III

Figure 7:
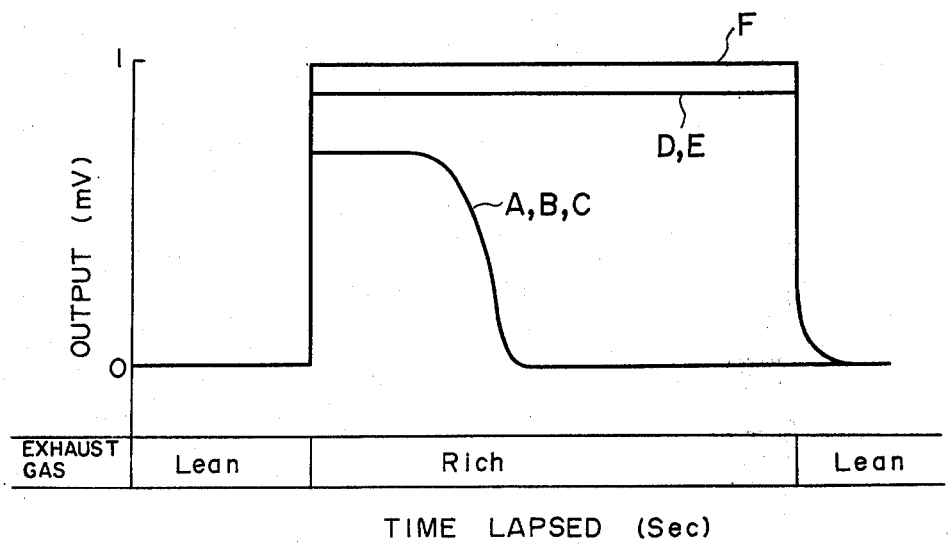
FIG. 7 is a graph showing the output characteristics of the oxygen sensors with respect to the condition of the exhaust gas to which the sensors are exposed.

Output characteristics of the oxygen sensors A, B, C, D, E and F were examined. The test was such made that the sensors A to F were disposed in a conduit through which two kinds of exhaust gas were alternately passed, one of which was a gas richer than stoichiometric and the other of which was a gas leaner than stoichiometric. The result is shown by the graph of FIG. 7. As is seen from this graph, the oxygen sensors A, B and C produced by the conventional method showed an undesired result wherein the electromotive force thereof was considerably low as compared with that of the sensors D, E and F produced by the method of the present invention, and the electromotive force thereof dropped rapidly to zero level even when the richer exhaust gas which has sufficient amount of oxygen to cause generation of electromotive force (EMF) of the sensors was present. It was found that the rapid drop in electromotive force of the sensors was originated from formation of cracks in the solid electrolyte layers of the sensors A, B and C. While, in the oxygen sensors D, E and F produced by the method of the invention, such problems were not recognized.

What is claimed is:

1. A method of producing a flat film type oxygen sensor including an oxygen ion conductive solid electrolyte layer, comprising the steps of:
    (a) preparing an electrode layer which has been fired;
    (b) preparing first and second electrolyte pastes each containing stabilizer, the amount of stabilizer in said first electrolyte paste being less than that in said second electrolyte paste;
    (c) applying said first electrolyte paste onto said electrode layer and then applying said second electrolyte paste onto the outer surface of said first electrolyte paste to form a layered paste heap on said electrode layer; and
    (d) air drying and then firing said layered paste heap to form a solid electrolyte layer on said electrode layer.

2. A method as claimed in claim 1, further comprising (e) before the step (c), preparing a third electrolyte paste containing stabilizer the amount of which is greater than that of said first electrolyte paste but less than that of said second electrolyte paste, said third electrolyte paste being applied onto the outer face of said first electrolyte paste prior to the application of said second electrolyte paste onto said first electrolyte paste.

3. A method as claimed in claim 1, in which said each of said first and second electrolyte pastes is composed of a certain amount of powdered $Y_2O_3$-$ZrO_2$ and a certain amount of organic vehicle, $Y_2O_3$ being the stabilizer.

4. A method as claimed in claim 1, in which each of said first and second electrolyte pastes is composed of a certain amount of powdered $CaO$-$ZrO_2$ and a certain amount of organic vehicle, $CaO$ being the stabilizer.

5. A method as claimed in claim 1, in which each of said first and second electrolyte pastes is composed of a certain amount of powdered $MgO$-$ZrO_2$ and a certain amount of organic vehicle, $MgO$ being the stabilizer.

6. A method as claimed in any of claims 1, 3, 4 or 5, in which the content of stabilizer in each paste is such determined that upon completion of the drying and firing process (d), the solid electrolyte layer thus produced contains from approximately 2% to approximately 23% stabilizer by weight.

7. A method as claimed in any of claims 3, 4 or 5, in which said organic vehicle is a mixture of ethylcellulose and terpineoil.

8. A method as claimed in claim 1, further comprising, during the step (c), (f) applying the same paste as said first electrolyte paste onto the outer surface of the prior applied first electrolyte paste prior to the application of said second electrolyte paste to said first electrolyte paste.

9. A method of producing a flat film type oxygen sensor including an oxygen ion conductive solid electrolyte layer, comprising the steps of:

(a) preparing first, second and third electrolyte pastes each containing stabilizer, the amount of stabilizer in said second electrolyte paste being greater than that in said first electrolyte paste but less than that in said third electrolyte; and (b) applying said first electrolyte paste onto an electrode layer, then applying said second layer electrolyte paste onto the outer surface of said first electrolyte paste, and then applying said third electrolyte paste onto the outer surface of said second electrolyte paste to form a layered paste application on said electrode layer; and (c) air-drying and firing said layered paste application to form a solid electrolyte layer on said electrode layer.

10. A method as claimed in claim 9, in which each of said first, second and third electrolyte pastes is comprised of an amount of powdered $Y_2O_3$-$ZrO_2$ and an amount of organic vehicle, $Y_2O_3$ being the stabilizer.

11. A method as claimed in claim 9, in which each of said first, second and third electrolyte pastes is comprised of an amount of powdered $CaO$-$ZrO_2$ and an amount of organic vehicle, $CaO$ being the stabilizer.

12. A method as claimed in claim 9, in which each of said first, second and third electrolyte pastes is comprised of an amount of powdered $MgO$-$ZrO_2$ and an amount of organic vehicle, $MgO$ being the stabilizer.

13. A method as claimed in any one of claims 9, 10, 11 or 12, in which the content of stabilizer in each paste is determined so that upon completion of the air-drying and firing process (c), the solid electrolyte layer thus produced contains from approximately 2% to approximately 23% stabilizer by weight.

14. A method as claimed in any of of claims 10, 11 or 12, in which said organic vehicle comprises a mixture of ethylcellulose and termpine oil.

* * * * *